United States Patent
Miller

(10) Patent No.: US 8,809,064 B2
(45) Date of Patent: Aug. 19, 2014

(54) SENSING HYDROXYL RADICALS IN OZONE WASHING SYSTEMS

(75) Inventor: Seth Miller, Englewood, CO (US)

(73) Assignee: Empire Technology Development LLC, Wilmington, DE (US)

(*) Notice: Subject to any disclaimer, the term of this patent is extended or adjusted under 35 U.S.C. 154(b) by 75 days.

(21) Appl. No.: 13/318,398

(22) PCT Filed: Mar. 9, 2011

(86) PCT No.: PCT/US2011/027741
§ 371 (c)(1),
(2), (4) Date: Nov. 1, 2011

(87) PCT Pub. No.: WO2012/121721
PCT Pub. Date: Sep. 13, 2012

(65) Prior Publication Data
US 2012/0231549 A1  Sep. 13, 2012

(51) Int. Cl.
*G01N 21/64* (2006.01)
*G01N 21/00* (2006.01)

(52) U.S. Cl.
USPC ....... 436/133; 436/127; 422/82.05; 422/68.1; 422/50

(58) Field of Classification Search
CPC ..... G01N 21/64; G01N 21/00; G01N 21/643; D06F 33/00
USPC ........... 436/131, 127; 422/82.05, 82.08, 68.1, 422/50
See application file for complete search history.

(56) References Cited

U.S. PATENT DOCUMENTS

| | | |
|---|---|---|
| 2004/0112838 A1 | 6/2004 | Martin |
| 2007/0119762 A1 | 5/2007 | Shao et al. |
| 2008/0003687 A1 | 1/2008 | Satoh et al. |

FOREIGN PATENT DOCUMENTS

WO    2007143785 A1    12/2007

OTHER PUBLICATIONS

United States Patent and Trademark Office, International Search Report and Written Opinion of the International Searching Authority for PCT/US11/27741, prepared on Aug. 29, 2011 and mailed on Sep. 6, 2011.
Colbert, Singapore waterless washing machine, Every Joe Technology, Nov. 21, 2005, accessed online on Oct. 18, 2011 via http://everyjoe.com/technology/singapore-waterless-washing-machine/?utm_source=everyjoe&utm_medium=web&utm_campaign=b5hubs_migration.
Ozone Laundry Systems, Dry ozone textile systems, Sandy, Utah, accessed online on Oct. 18, 2011 via http://www.ozonelaundrysystems.com/images/DryOzoneTextileSystemsFlyer.pdf.

(Continued)

*Primary Examiner* — Christine T Mui
(74) *Attorney, Agent, or Firm* — Turk IP Law, LLC

(57) ABSTRACT

Implementations and techniques for sensing hydroxyl radicals in ozone washing systems are generally disclosed. In some examples, the disclosure describes an ozone washing system having an ozone reservoir coupled to a washing machine and a control unit configured to direct the insertion of ozone from the ozone reservoir to the washing machine based on sensed hydroxyl radical levels in fluid samples from the washing machine.

25 Claims, 5 Drawing Sheets

(56) References Cited

OTHER PUBLICATIONS

Aquawing Ozone Injection Systems, Aquawing vs. Charge, 2010, accessed online on Oct. 18, 2011 via http://www.aquawingozone.com/education/charge.html.

Laundry Consulting, Benefits of ozone laundry, 2008, accessed online on Oct. 18, 2011 via http://laundryconsulting.com/solution/benefits-of-ozone-laundry/.

Floyd, Robert A. et al., Sensitive assay of hydroxyl free radical formation utilizing high pressure liquid chromatography with electrochemical detection of phenol and solicylate hydroxylation products, Journal of Biochemical and Biophysical Methods, vol. 10, Issues 3-4, Dec. 1984, pp. 221-235.

Freinbichler, Wolfhardt et al, The detection of hydroxyl radicals in vivo, Journal of Inorganic Biochemistry, vol. 102, Issues 5-6, May 2008, pp. 1329-1333.

Fang, Xingwang et al, OH radical formation by ultrasound in aqueous solutions Part I: the chemistry underlying the terephthalate dosimeter, Ultrasonics Sonochemistry, vol. 3, Issue 1, Feb. 1996, pp. 57-63.

Allegre, C. et al., Treatment and reuse of reactive dyeing effluents, Journal of Membrane Science, vol. 269, Issues 1-2, Feb. 1, 2006, pp. 15-34.

Aquawing Ozone Injection Systems, Ozone Facts vs. Fallacies, 2010, accessed online on Oct. 18, 2011 via http://www.aquawingozone.com/education/fallacy.html.

Wikipedia, PolyAPTAC, last modified on Jul. 9, 2007, accessed online on Oct. 18, 2011 via http://en.wikipedia.org/wiki/PolyAPTAC.

Wikipedia, PolyAPTAC, last modified on Jun. 19, 2012, accessed online on Oct. 15, 2012 via http://en.wikipedia.org/wiki/PolyAPTAC.

International Preliminary Report on Patentability PCT/US2011/027741, mailed Sep. 19, 2013.

400 A computer program product.

402 A signal bearing medium.

404 Machine-readable instructions, which, if executed by one or more processors, operatively enable a computing device to:
 obtain and treat one or more samples of fluid from a washing machine, wherein the treatment includes reducing turbidity via a filter and removing soluble dye molecules via a large molecule sieve;
 deliver, via an indicator reservoir coupled in communication with the test chamber, a hydroxyl radical indicator to the one or more samples of fluid, wherein the hydroxyl radical indicator is sensitive to oxidization in the presence of hydroxyl radicals;
 quantify hydroxyl radical levels in the one or more samples of fluid; and/or
 insert ozone, via an ozone reservoir, to the washing machine based at least in part on the quantification of the hydroxyl radical levels.

| 406 a computer-readable medium. | 408 a recordable medium. | 410 a communications medium. |

Fig. 4

SENSING HYDROXYL RADICALS IN OZONE WASHING SYSTEMS

CROSS-REFERENCE TO RELATED APPLICATIONS

The present application is a U.S. national stage application claiming the benefit of International Application No. PCT/US2011/027741, filed on Mar. 9, 2011, the entire contents of which are incorporated herein by reference.

BACKGROUND

Unless otherwise indicated herein, the approaches described in this section are not prior art to the claims in this application and are not admitted to be prior art by inclusion in this section.

In ozone washing machines, ozone may be injected into a washing drum at predetermined injection quantities. However, measuring the actual concentration of ozone in wash systems may be complex. Accordingly, such predetermined injection quantities may often be poorly correlated with the actual amount of cleaning that takes place.

SUMMARY

Some example methods, apparatus, and systems related to sensing hydroxyl radicals may be implemented via an ozone washing system. Such an ozone washing system may include a washing machine, an ozone reservoir, a hydroxyl radical sensor, and/or a control unit. The ozone reservoir may be coupled in fluid communication with the washing machine. The hydroxyl radical sensor may be coupled in fluid communication with the washing machine. The hydroxyl radical sensor may be configured to quantify hydroxyl radical levels in one or more samples of fluid from the washing machine. The hydroxyl radical sensor may be sensitive to oxidization in the presence of hydroxyl radicals. The control unit may be operatively associated with the hydroxyl radical sensor. The control unit may be configured to direct the insertion of ozone associated with the ozone reservoir to the washing machine based at least in part on the sensed hydroxyl radical levels.

Some example methods, apparatus, and systems related to sensing hydroxyl radicals in ozone washing systems may be implemented via a hydroxyl radical sensor. Such a hydroxyl radical sensor may include a filter, a large molecule sieve, a test chamber, and/or an indicator reservoir. The filter may be configured to reduce turbidity in one or more samples of fluid. The large molecule sieve may be coupled in fluid communication with the filter. The large molecule sieve may be configured to remove soluble dye molecules from the one or more samples of fluid. The test chamber may be coupled in fluid communication with the large molecule sieve. The test chamber may be configured to receive the one or more samples of fluid. The indicator reservoir may be coupled in communication with the test chamber to deliver a hydroxyl radical indicator to the test chamber. The hydroxyl radical indicator may be sensitive to oxidization in the presence of hydroxyl radicals. The hydroxyl radical sensor may be configured to quantify hydroxyl radical levels in the one or more samples of fluid.

Some example methods, apparatus, and systems related to sensing hydroxyl radicals in ozone washing systems may be implemented via a method of quantifying hydroxyl radical levels in a washing machine. Such a method may include obtaining one or more samples of fluid from the washing machine. Turbidity may be reduced, via a filter, in the one or more samples of fluid. Soluble dye molecules may be removed, via a large molecule sieve coupled in fluid communication with the filter, in the one or more samples of fluid. The one or more samples of fluid may be received, via a test chamber coupled in fluid communication with the large molecule sieve. A hydroxyl radical indicator may be delivered, via an indicator reservoir coupled in communication with the test chamber, to the test chamber. The hydroxyl radical indicator may be sensitive to oxidization in the presence of hydroxyl radicals. Hydroxyl radical levels may be quantified in the one or more samples of fluid.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

FIG. 4 is an illustration of an example computer program product; and

DETAILED DESCRIPTION

Figure 1:
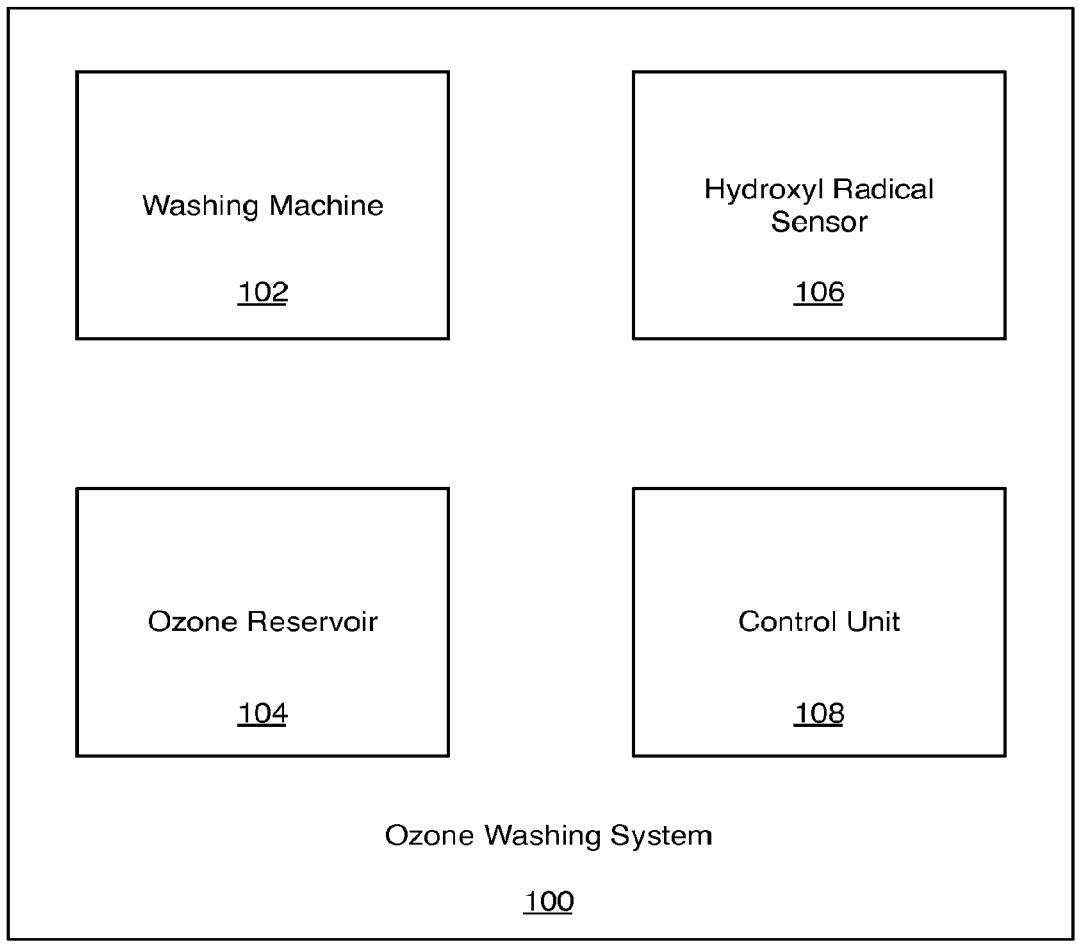
FIG. 1 a block diagram illustrating an example ozone washing system including a hydroxyl radical sensor.

The following description sets forth various examples along with specific details to provide a thorough understanding of claimed subject matter. It will be understood by those skilled in the art, however that claimed subject matter may be practiced without some or more of the specific details disclosed herein. Further, in some circumstances, well-known methods, procedures, systems, components and/or circuits have not been described in detail in order to avoid unnecessarily obscuring claimed subject matter.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

Methods, apparatus, and systems related to sensing hydroxyl radicals in ozone washing systems are described.

In an ozone washing systems, ozone may be injected into the washing drum at known quantities, but this injection level may be often poorly correlated with the actual amount of cleaning that takes place. There may be several reasons for this limitation, one of which is that the actual active cleaning species is hydroxyl radicals, which form from ozone at high pH (e.g., in laundry, detergents may keep the pH above ten). The rate of formation of hydroxyl radicals may be highly dependent on the specific chemistry in the laundry load, as well as on such unexpected factors as the amount of turbulence in the system. One way to compensate for this today is for machines to either generate extra ozone—which may cause unwanted color fading—or to operate below the optimum ozone level. A process that may improve the consistency and effectiveness of the wash provided by an ozone laundry system by measuring hydroxyl radical activity is discussed below.

Such a process may be used to quantitate the concentration of hydroxyl radicals present in an ozone washing machine in real time or near real time. The sampling and quantitation may be performed at regular intervals or at irregular intervals. For example, sampling and quantitation may be performed every 5 minutes, every 10 minutes, every 15 minutes, every 30 minutes, and so on. Alternatively, sampling and quantitation may be performed at random intervals. In yet another alternative, the sampling and quantitation interval may vary depending upon the previously determined concentration of hydroxyl radicals, where a high previous concentration may result in a longer time interval, and a low previous concentration may result in a shorter time interval until the next sampling and quantitation.

The samples may be optionally treated prior to measurement of hydroxyl radicals. For example, a sample of fluid may be taken from the washing machine, and may be pre-processed to remove particles to clarify the sample and to remove large molecules including dye molecules. This clarified sample may be exposed to a hydroxyl radical indicator (for example, terephthalic acid, which reacts with hydroxyl radicals to form 2-hydroxyterephthalate, a highly fluorescent molecule whose fluorescence is measurable at concentrations as low as five hundred picomolar (pM)). This may allow real-time spectroscopic determination of the laundering action of ozone, so that ozone injection may be increased or reduced in concert with the needs of the wash load. Other hydroxyl radical indicators may include 4-hydroxybenzoic acid, salicylate, phenylalanine, the like, and/or combinations thereof.

FIG. 1 a block diagram illustrating an example ozone washing system 100 arranged in accordance with at least some embodiments of the present disclosure. In the illustrated example, such an ozone washing system 100 may include a washing machine 102, an ozone reservoir 104, a hydroxyl radical sensor 106, and/or a control unit 108. Ozone reservoir 104 may be coupled in fluid communication with washing machine 102.

Hydroxyl radical sensor 106 may be coupled in fluid communication with washing machine 102. Hydroxyl radical sensor 106 may be configured to quantify hydroxyl radical levels in one or more samples of fluid from washing machine 102. Hydroxyl radical sensor 106 may be sensitive to oxidization in the presence of hydroxyl radicals.

Control unit 108 may be operatively associated with hydroxyl radical sensor 106. Control unit 108 may be configured to direct the insertion of ozone associated with ozone reservoir 102 to washing machine 102 based at least in part on the sensed hydroxyl radical levels.

In some examples, hydroxyl radical sensor 106 may use a hydroxyl radical indicator that may be sensitive to oxidization in the presence of hydroxyl radicals. Such a hydroxyl radical indicator may be sensitive to oxidization in the presence of hydroxyl radicals to form a fluorescent molecule, where the hydroxyl radical indicator is either non-fluorescent or less fluorescent prior to oxidation. Additionally or alternatively, such a hydroxyl radical indicator may be sensitive to oxidization in the presence of hydroxyl radicals while being non-sensitive to oxidization in the presence of ozone (for example, substantially less sensitive or completely insensitive to oxidization in the presence of ozone than in the presence of hydroxyl radicals). In some examples, such a hydroxyl radical indicator may include terephthalate. In other examples, such a hydroxyl radical indicator may include 4-hydroxybenzoic acid, salicylate, phenylalanine, the like, and/or combinations thereof. For example, terephthalate may not be converted to the fluorescent hydroxyterephthalate by weak oxidants such as hypochlorite (bleach), and such a hydroxyl radical indicator may be selective for hydroxyl radicals. Terephthalate oxidation may be relatively insensitive to those oxidants that have far lower oxidation potentials than hydroxyl radicals, where such oxidants may be unable to convert terephthalate to fluorescent hydroxyterephthalate. Conversely, other methods of measuring ozone concentration may be confounded by other oxidants (such as, hypochlorite in bleach), and are therefore may not suited for in situ measurements of ozone wash water.

Additionally or alternatively, such a hydroxyl radical indicator may have low toxicity or be non-toxic (e.g., safe for usage in quantities suitable for hydroxyl radical sensor 106 without being a known or suspected health hazard). In some examples, such a hydroxyl radical indicator may include terephthalate. For example, terephthalate is generally considered to be non-toxic (e.g., terephthalate is a component of polyethylene terephthalate (PET) plastics), and therefore not a health hazard when used. Other substances that are capable of performing some or all of the above functions may be used for or included in such a hydroxyl radical indicator. If the hydroxyl radical indicator is toxic or suspected of being toxic, a skilled operator can exercise a reasonable degree of care in handling the material. Additionally, the ozone washing system can easily be designed to isolate the hydroxyl radical indicator to prevent exposure to the potentially toxic material.

For ozone laundry cleaning, hydroxyl radicals rather than ozone itself are responsible for the superior cleaning properties. For example, ozone laundry systems become very effective at cleaning linens once dissolved ozone concentrations reach 1.5 to 3.0 ppm (parts per million). This effectiveness may be directly related to the ability of ozone to create OH radicals (hydroxyl radicals) with small amounts of alkali. In some examples, the methods, apparatus, and systems related to sensing hydroxyl radicals in ozone washing systems discussed herein, therefore, may monitor hydroxyl radical concentrations, rather than monitoring ozone itself.

Accordingly, a fluorescent detection system (as will be described in greater detail with regard to FIG. 2 below) may be used for monitoring hydroxyl radical concentration in an ozone washing machine 102. In examples using terephthalate to react with the hydroxyl radicals, measurements of fluorescence from the resulting hydroxyterephalate may be used to quantitate hydroxyl radical concentration. Ozone and terephthalate are not fluorescent. Excitation of hydroxyterephalate at a 315 nm wavelength produces a fluorescent emission at a wavelength of 435 nm. The total fluorescence may be linearly dependent on the concentration of added hydroxyl radicals, and may not be dependent on terephthalate concentration when the hydroxyl radical is the limiting reagent. It may be possible to detect the formation of hydroxyterephthalate product at about 500 μM (0.5 nM) concentrations, or the like.

However, direct application of a hydroxyl radical indicator to a sample of fluid from ozone washing machine 102 may not be particularly effective to quantitate the hydroxyl radical concentration possibly due to the presence of interfering materials. For example, a hydroxyl radical indicator may react with other compounds in the sample of fluid obtained from ozone washing machine 102, such as detergents, brighteners, soils, the like, and/or combinations thereof, which may complicate measurements of fluorescence. Additionally or alternatively, the turbidity of a sample of fluid from ozone washing machine 102 may also limit or complicate the ability to take accurate measurements with the direct application of a hydroxyl radical indicator to the sample of fluid. As used herein the term "turbidity" may refer to the presence of particulates that may cloud a fluid. Accordingly, as will be described in greater detail below, a sample of fluid from ozone washing machine 102 may be preconditioned or pretreated prior to application of a hydroxyl radical indicator.

In operation, ozone washing system 100 may be primarily sensitive to hydroxyl radials as compared to other oxidants, making it a selective means for detecting ozone effectiveness in the wash. Conversely, some conventional methods of measuring ozone concentration may be confounded by the presence of other oxidants.

Figure 2:
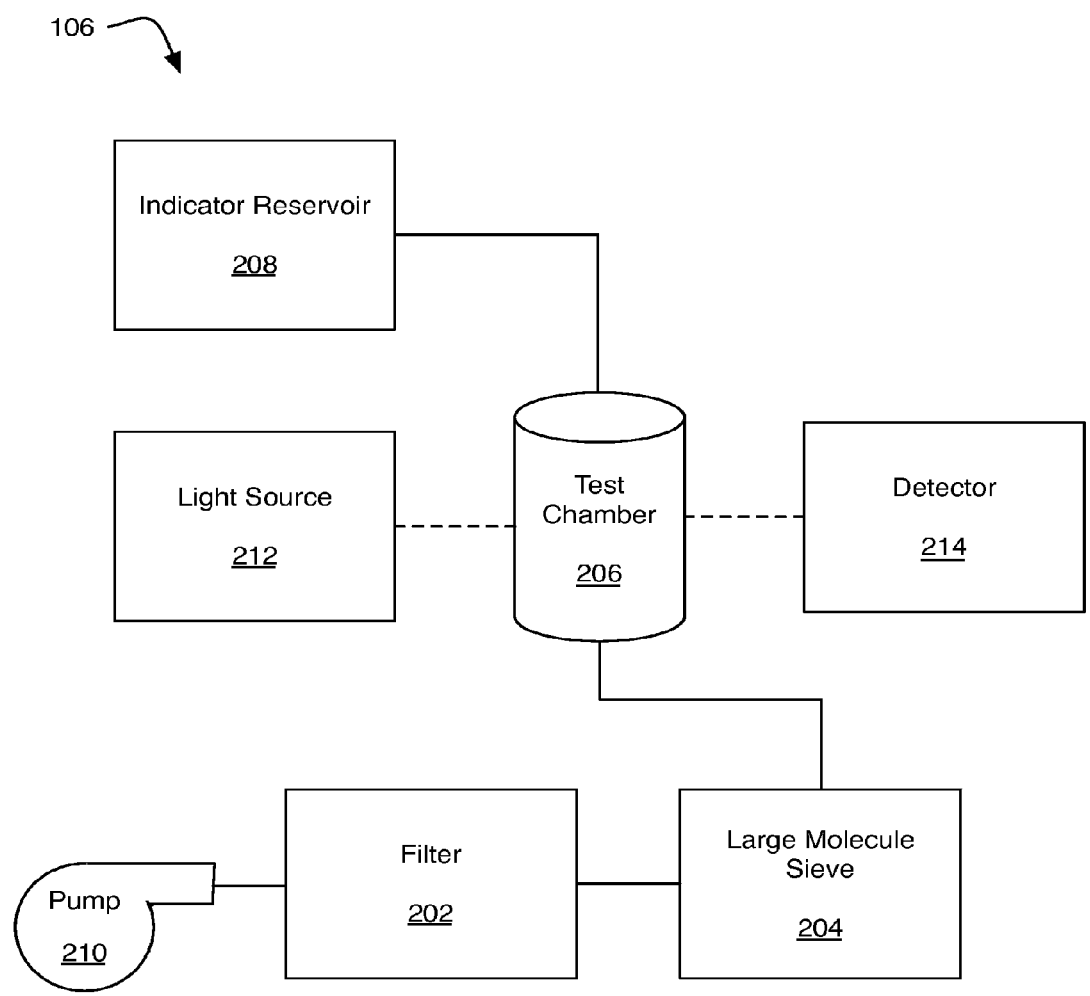
FIG. 2 is a block diagram illustrating an example hydroxyl radical sensor.

FIG. 2 is a block diagram illustrating an example hydroxyl radical sensor 106 arranged in accordance with at least some embodiments of the present disclosure. In the illustrated example, such a hydroxyl radical sensor 106 may include a filter 202, a large molecule sieve 204, a test chamber 206, and/or an indicator reservoir 208.

Filter 202 may be configured to reduce turbidity in one or more samples of fluid. Filter 202 may include one or more of a polymer filter, a ceramic filter, a porous metal filter, the like, and/or combinations thereof. For example, filter 202 may include one or more of a PVDF-type polymer filter, a silicon dioxide-type ceramic filter, a stainless steel-type porous metal filter (e.g., a porous metal filter coated with polymer), the like, and/or combinations thereof. In some examples, filter 202 may be a micro-porous-type filter. For example, a sample of fluid of wash water may be passed through a micro-porous-type filter 202 to remove fine particles and reduce turbidity. A PVDF-type polymer filter is one example of a micro-porous-type filter 202 material that may be stable in the presence of ozone.

Large molecule sieve 204 may be coupled in fluid communication with filter 202. Large molecule sieve 204 may be configured to remove soluble dye molecules from the one or more samples of fluid. Large molecule sieve 204 may include one or more sieves of an inorganic sieve, a polymeric sieve, the like, and/or combinations thereof. For example, large molecule sieve 204 may include one or more of a silica-type inorganic sieve (e.g., silicon dioxide, with a chemical formula of $SiO_2$), an alumina-type inorganic sieve (e.g., aluminium (III) oxide, with a chemical formula of $Al_2O_3$), an ion-exchange resin-type polymeric sieve (e.g., an Amberlite™-type sieve), a polyAPTAC-type polymeric sieve (e.g., poly(acrylamido-N-propyltrimethylammonium chloride)), a ceramic-type ultra-filtration membrane, a ceramic-type nano-filtration membrane, a PVDF-type polymer ultra-filtration membrane, a PVDF-type polymer nano-filtration membrane, the like, and/or combinations thereof. For example, large molecule sieve 204 may be used to pass a sample of fluid a sorbent and/or ion exchange type material to remove soluble dye molecules (e.g., fluorescent brighteners or the like). Such dye molecules may typically include polyions (e.g., Calcofluor), which may adhere irreversibly to inorganic sorbents (e.g., silica, alumina, or to polymeric materials such as Amberlite or PolyAPTAC). Accordingly, large molecule sieve 204 may remove components that might compete with the fluorescence produced by the hydroxyl radical indicator (e.g., hydroxyterephthalate), and thereby degrade the signal-noise ratio of the measurement quantifying hydroxyl radicals.

Test chamber 206 may be coupled in fluid communication with large molecule sieve 204. Test chamber 206 may be configured to receive the one or more samples of fluid. Additionally or alternatively, test chamber 206 may include a preliminary test chamber that may be configured to hold the one or more samples without the hydroxyl radical indicator for a pre-indicator control measurement, and a primary test chamber that may be configured to hold the one or more samples with the hydroxyl radical indicator for a post-indicator measurement.

Indicator reservoir 208 may be coupled in communication with test chamber 206 to deliver a hydroxyl radical indicator to test chamber 206. The hydroxyl radical indicator may be sensitive to oxidization in the presence of hydroxyl radicals. Hydroxyl radical sensor 106 may be configured to quantify hydroxyl radical levels in the one or more samples of fluid.

Additionally or alternatively, hydroxyl radical sensor 106 may include a pump 210, a light source 212, and/or a detector 214. Pump 210 may be coupled in fluid communication with filter 202.

Light source 212 and detector 214 may be associated with test chamber 206. Light source 212 and detector 214 may be configured to perform a spectroscopic measurement on the one or more samples of fluid received in test chamber 206. For example, an ultraviolet light-emitting diode-type light source 212 (UV LED) may be associated with a charge-coupled device-type detector 214 (CCD) for fluorescence detection, although other suitable light source 212 and/or detector 214 may be used.

Hydroxyl radical sensor 106 may be directed via control unit 108 (FIG. 1). Additionally or alternatively, hydroxyl radical sensor 106 may include an independent control unit (not shown) that is distinct from control unit 108.

Figure 3:
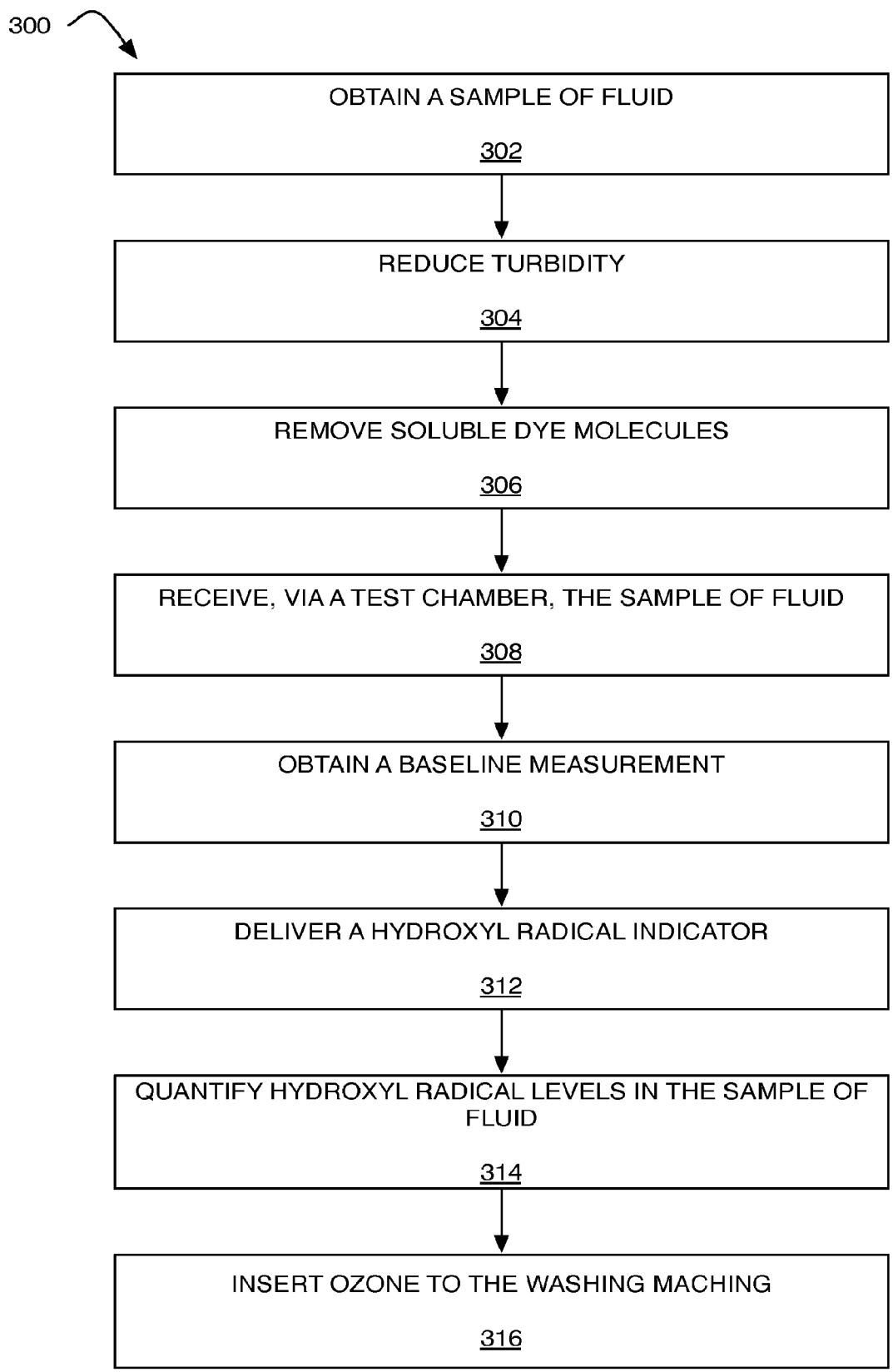
FIG. 3 is an illustration of an example process for operation of a hydroxyl radical sensor.

FIG. 3 is an illustration of an example process for operation of a hydroxyl radical sensor arranged in accordance with at least some embodiments of the present disclosure. In the illustrated example, process 300, and other processes described herein, set forth various functional blocks or actions that may be described as processing steps, functional operations, events and/or acts, etc., which may be performed by hardware, software, and/or firmware. Those skilled in the art in light of the present disclosure will recognize that numerous alternatives to the functional blocks shown in FIG. 3 may be practiced in various implementations. For example, although process 300, as shown in FIG. 3, comprises one particular order of blocks or actions, the order in which these blocks or actions are presented does not necessarily limit claimed subject matter to any particular order. Likewise, intervening actions not shown in FIG. 3 and/or additional actions not shown in FIG. 3 may be employed and/or some of the actions shown in FIG. 3 may be eliminated, without departing from the scope of claimed subject matter. Process 300 may include one or more of operations as illustrated by blocks 302, 304, 306, 308, 310, 312, 314, and/or 316.

As illustrated, process 300 may be implemented for operation of a hydroxyl radical sensor during operation of an ozone washing system. Processing may begin at operation 302, "obtain a sample of fluid", where a sample of fluid may be obtained. For example, one or more samples of fluid may be obtained from an ozone washing system. In some examples, the obtaining of the one or more samples of fluid may be performed via a pump coupled in fluid communication with the filter and the washing machine. An exemplary sample size may be about one milliliter, or the like. Small volume samples relative to the total volume of the ozone washing system allows one or more samplings to be performed without significantly impacting the laundry being cleaned.

Processing may continue from operation 302 to operation 304, "reduce turbidity", where turbidity may be reduced. For example, turbidity may be reduced in the one or more samples of fluid via a filter. This operation may remove particles associated with the turbidity of a sample of fluid, where such particles may limit the ability to take an accurate measurement quantifying hydroxyl radicals. Alternatively, a centrifuge can be used in place of or in addition to the filter to separate suspended particles from the sample.

Processing may continue from operation 304 to operation 306, "remove soluble dye molecules", where soluble dye molecules may be removed. For example, soluble dye molecules may be removed, via a large molecule sieve coupled in fluid communication with the filter, in the one or more samples of fluid. This operation may remove components that might compete with the fluorescence produced by the hydroxyl radical indicator (e.g., hydroxyterephthalate), and thereby degrade the signal-noise ratio of a measurement quantifying hydroxyl radicals.

Processing may continue from operation 306 to operation 308, "receive, via a test chamber, the sample of fluid", where the sample of fluid may be received via a test chamber. For example, the one or more samples of fluid may be received, via a test chamber coupled in fluid communication with the large molecule sieve.

Processing may continue from operation 308 to operation 310, "obtain a baseline measurement", where a baseline measurement may be obtained. For example, a baseline measurement of the fluorescence of a sample of fluid may be obtained prior to delivery of the hydroxyl radical indicator. Such a baseline measurement may be used as a control measurement of the sample to quantitate the background fluorescence from other molecules. Additionally or alternatively, an alternative baseline measurement may be obtained prior to delivery of the hydroxyl radical indicator. Such an alternative baseline measurement may include doping a sample of fluid with a known quantity of hydroxyterephthalate or the like. Such an alternative baseline measurement may be used as a control measurement of the sample to account for remaining particles that may cause turbidity and/or to quantitate the background fluorescence from other molecules. Such an alternative baseline measurement may be used in place of the baseline measurement describe above, or may be used in combination with the baseline measurement describe above.

Processing may continue from operation 310 to operation 312, "deliver a hydroxyl radical indicator", where a hydroxyl radical indicator may be delivered to the sample of fluid. For example, a hydroxyl radical indicator may be delivered, via an indicator reservoir coupled in communication with the test chamber, to the test chamber. In examples where terephthalate is used as the hydroxyl radical indicator, about one micromole of terephthalate (e.g., about 166 µg) may be added to a 1 milliliter sample to form an approximately one millimolar (mM) solution in the sample chamber, although the amount may vary depending on the sample size. In such an example, one gram of terephthalate may last for over one thousand loads. Terephthalate is typically a powder, but it is highly soluble in basic water, and may be most easily dispensed as a concentrated solution (for example, about 1 mM, about 5 mM, about ten mM, or greater). After delivery of the hydroxyl radical indicator, the sample may be optionally stirred, mixed, agitated, shaken, or otherwise treated to distribute the hydroxyl radical indicator within the sample.

Processing may continue from operation 312 to operation 314, "quantify hydroxyl radical levels in the sample of fluid", where hydroxyl radical levels may be quantified in the sample of fluid. For example, hydroxyl radical levels may be quantified in the one or more samples of fluid based at least in part on a measure of fluorescence. In examples where a baseline measurement is taken, the quantification of the hydroxyl radical levels may be based at least in part on the taken baseline measurement. In such an example, a calculation of the difference in fluorescence between the taken baseline measurement and the hydroxyl radical indicator measurement may be directly proportional to hydroxyl radical concentration. In some examples, the difference in fluorescence and/or the calculated hydroxyl radical concentration may be displayed or recorded. In some examples, the quantification of the hydroxyl radical levels may be performed via a light source and a detector associated with the test chamber. Additionally or alternatively, the sample of fluid may be allowed to equilibrate between the delivery of a hydroxyl radical indicator and the quantification of hydroxyl radical levels for a period of time, such as about 5 seconds, about 10 seconds, about 20 seconds, about 30 seconds, or about 60 seconds. After quantitation of the sample, the sample can be disposed of or stored in a waste storage container for subsequent removal and disposal.

In some examples the obtaining of the one or more samples and/or the quantification of hydroxyl radical levels may be performed at intervals. Such intervals may be determined based at least in part on a previous quantification of hydroxyl radical levels. Additionally or alternatively, such intervals may be set as regular intervals or at irregular intervals.

Processing may continue from operation 314 to operation 316, "insert ozone to the washing machine", where ozone may be inserted into the washing machine if needed or desired. For example, ozone may be inserted into the washing machine, via an ozone reservoir, based at least in part on the quantification of the hydroxyl radical levels. Accordingly, additional ozone may be added to a washing machine where the quantification of the hydroxyl radical levels indicate a less than optimal (or desirable) level of hydroxyl radicals.

In operation, process 300 may permit real-time (or near real-time) measurements of hydroxyl radical concentration in samples of wash water for ozone washing machines. Such real-time measurements of hydroxyl radical concentration may be used to adjust the usage of ozone in the associated washing machine.

FIG. 4 illustrates an example computer program product 400 that is arranged in accordance with at least some embodiments of the present disclosure. Computer program product 400 may include a signal bearing medium 402. Signal bearing medium 402 may include one or more machine-readable instructions 404, which, when executed by one or more processors, may operatively enable a computing device to provide the functionality described above with respect to FIG. 3. Thus, for example, referring to the ozone washing system 100 of FIG. 1 and/or hydroxyl radical sensor 106 of FIG. 2 may undertake one or more of the actions shown in FIG. 3 in response to instructions 404 conveyed by medium 402.

In some implementations, signal bearing medium 402 may encompass a computer-readable medium 406, such as, but not limited to, a hard disk drive, a Compact Disc (CD), a Digital Video Disk (DVD), a digital tape, memory, etc. In some implementations, signal bearing medium 402 may encompass a recordable medium 408, such as, but not limited to, memory, read/write (R/W) CDs, R/W DVDs, etc. In some implementations, signal bearing medium 402 may encompass a communications medium 410, such as, but not limited to, a digital and/or an analog communication medium (e.g., a fiber optic cable, a waveguide, a wired communication link, a wireless communication link, etc.).

Figure 5:
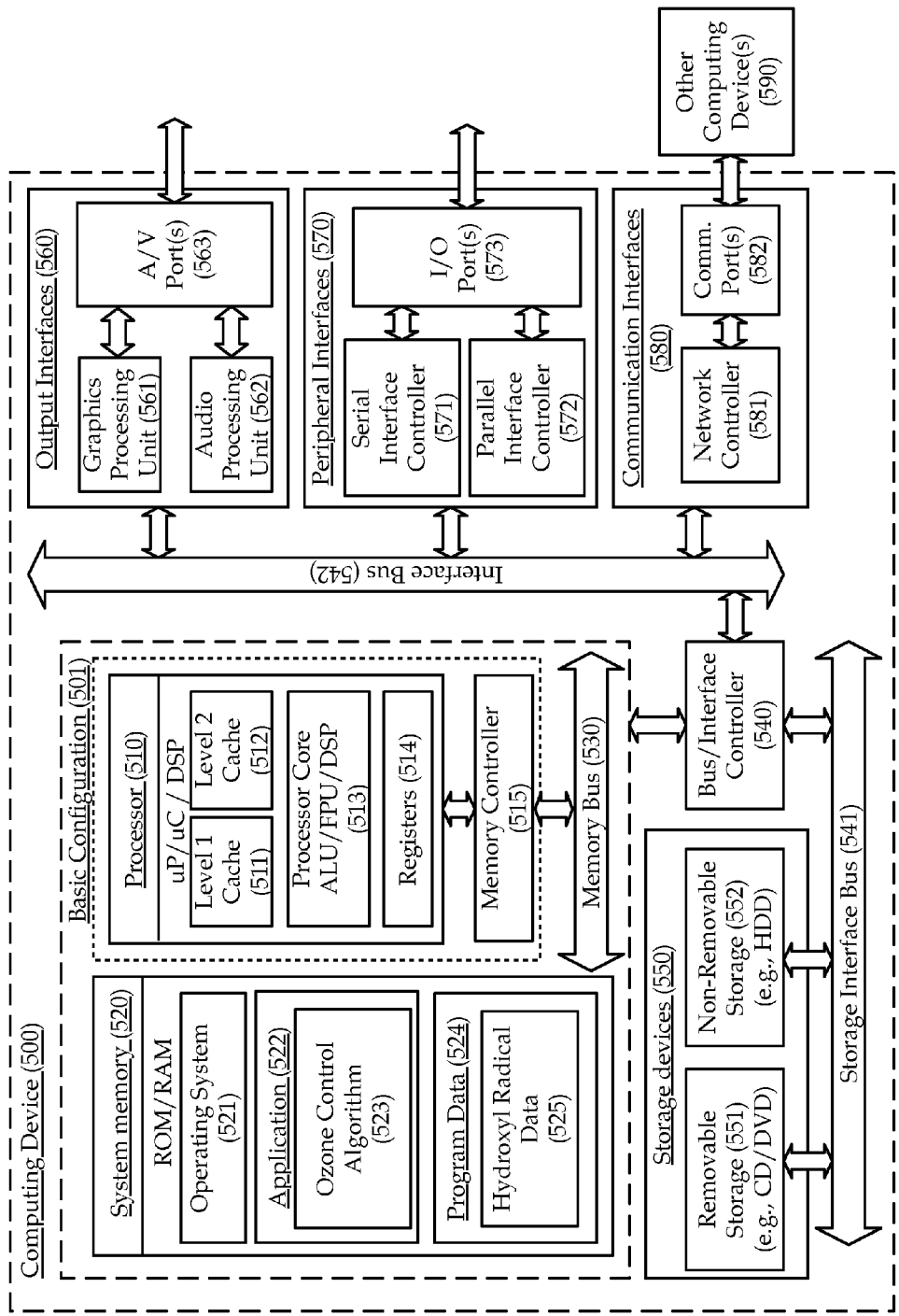
FIG. 5 is a block diagram illustrating an example computing device, all arranged in accordance with at least some embodiments of the present disclosure.

FIG. 5 is a block diagram illustrating an example computing device 500 that is arranged in accordance with at least some embodiments of the present disclosure. In one example basic configuration 501, computing device 500 may include one or more processors 510 and system memory 520. A memory bus 530 can be used for communicating between the processor 510 and the system memory 520.

Depending on the desired configuration, processor 510 may be of any type including but not limited to a microprocessor (µP), a microcontroller (µC), a digital signal processor (DSP), or any combination thereof. Processor 510 can include one or more levels of caching, such as a level one cache 511 and a level two cache 512, a processor core 513, and registers 514. The processor core 513 can include an arithmetic logic unit (ALU), a floating point unit (FPU), a digital signal processing core (DSP Core), or any combination thereof. A memory controller 515 can also be used with the processor 510, or in some implementations the memory controller 515 can be an internal part of the processor 510.

Depending on the desired configuration, the system memory 520 may be of any type including but not limited to volatile memory (such as RAM), non-volatile memory (such as ROM, flash memory, etc.) or any combination thereof. System memory 520 may include an operating system 521, one or more applications 522, and program data 524. Application 522 may include ozone control algorithm 523 that can be arranged to perform the functions, actions, and/or operations as described herein including the functional blocks, actions, and/or operations described with respect to process 300 of FIG. 3. Program Data 524 may include hydroxyl radical data 525 for use with the ozone control algorithm 523. In some example embodiments, application 522 may be arranged to operate with program data 524 on an operating system 521 such that implementations of management of ozone levels during operation of an ozone washing system may be provided as described herein. This described basic configuration is illustrated in FIG. 5 by those components within dashed line 501.

Computing device 500 may have additional features or functionality, and additional interfaces to facilitate communications between the basic configuration 501 and any required devices and interfaces. For example, a bus/interface controller 540 may be used to facilitate communications between the basic configuration 501 and one or more data storage devices 550 via a storage interface bus 541. The data storage devices 550 may be removable storage devices 551, non-removable storage devices 552, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 520, removable storage 551 and non-removable storage 552 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 500. Any such computer storage media may be part of device 500.

Computing device 500 may also include an interface bus 542 for facilitating communication from various interface devices (e.g., output interfaces, peripheral interfaces, and communication interfaces) to the basic configuration 501 via the bus/interface controller 540. Example output interfaces 560 may include a graphics processing unit 561 and an audio processing unit 562, which may be configured to communicate to various external devices such as a display or speakers via one or more A/V ports 563. Example peripheral interfaces 570 may include a serial interface controller 571 or a parallel interface controller 572, which may be configured to communicate with external devices such as input devices (e.g., keyboard, mouse, pen, voice input device, touch input device, etc.) or other peripheral devices (e.g., printer, scanner, etc.) via one or more I/O ports 573. An example communication interface 580 includes a network controller 581, which may be arranged to facilitate communications with one or more other computing devices 590 over a network communication via one or more communication ports 582. A communication connection is one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), infrared (IR) and other wireless media. The term computer readable media as used herein may include both storage media and communication media.

Computing device 500 may be implemented as a portion of a small-form factor portable (or mobile) electronic device such as a cell phone, a personal data assistant (PDA), a personal media player device, a wireless web-watch device, a personal headset device, an application specific device, or a hybrid device that includes any of the above functions. Computing device 500 may also be implemented as a personal computer including both laptop computer and non-laptop computer configurations. In addition, computing device 500 may be implemented as part of a wireless base station or other wireless system or device.

Some portions of the foregoing detailed description are presented in terms of algorithms or symbolic representations of operations on data bits or binary digital signals stored within a computing system memory, such as a computer memory. These algorithmic descriptions or representations are examples of techniques used by those of ordinary skill in the data processing arts to convey the substance of their work to others skilled in the art. An algorithm is here, and generally, is considered to be a self-consistent sequence of operations or similar processing leading to a desired result. In this context, operations or processing involve physical manipulation of physical quantities. Typically, although not necessarily, such quantities may take the form of electrical or magnetic signals capable of being stored, transferred, combined, compared or otherwise manipulated. It has proven convenient at times, principally for reasons of common usage, to refer to such signals as bits, data, values, elements, symbols, characters, terms, numbers, numerals or the like. It should be understood, however, that all of these and similar terms are to be associated with appropriate physical quantities and are merely convenient labels. Unless specifically stated otherwise, as apparent from the following discussion, it is appreciated that throughout this specification discussions using terms such as "processing," "computing," "calculating," "determining" or the like refer to actions or processes of a computing device, that manipulates or transforms data represented as physical electronic or magnetic quantities within memories, registers, or other information storage devices, transmission devices, or display devices of the computing device.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In some embodiments, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a flexible disk, a hard disk drive (HDD), a Compact Disc (CD), a Digital Video Disk (DVD), a digital tape, a computer memory, etc.; and a transmission type medium such as a digital and/or an analog communication medium (e.g., a fiber optic cable, a waveguide, a wired communication link, a wireless communication link, etc.).

The herein described subject matter sometimes illustrates different components contained within, or connected with, different other components. It is to be understood that such depicted architectures are merely examples and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While certain example techniques have been described and shown herein using various methods and systems, it should be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter not be limited to the particular examples disclosed, but that such claimed subject matter also may include all implementations falling within the scope of the appended claims, and equivalents thereof.

What is claimed is:

1. An ozone washing system, comprising:
    a washing machine;
    an ozone reservoir coupled in fluid communication with the washing machine;
    a hydroxyl radical sensor coupled in fluid communication with the washing machine, the hydroxyl radical sensor configured to quantify hydroxyl radical levels in one or more samples of fluid from the washing machine based on fluorescence of a hydroxyl radical indicator, wherein the hydroxyl radical sensor is sensitive to oxidization in the presence of hydroxyl radicals;
    a filter coupled in fluid communication with a large molecule sieve wherein the large molecule sieve is configured to remove from the one or more samples, soluble dye molecules comprising components that can compete with fluorescence produced by the hydroxyl radical indicator; and
    a control unit operatively associated with the hydroxyl radical sensor, the control unit configured to direct the insertion of ozone associated with the ozone reservoir to the washing machine based at least in part on the sensed hydroxyl radical levels.

2. The ozone washing system of claim 1, wherein the hydroxyl radical sensor further comprises:
    a test chamber coupled in fluid communication with the large molecule sieve, the test chamber configured to receive one or more samples of fluid from the washing machine; and
    an indicator reservoir coupled in communication with the test chamber to deliver the hydroxyl radical indicator to the test chamber, wherein the hydroxyl radical indicator is sensitive to oxidization in the presence of hydroxyl radicals;
    wherein the filter is configured to reduce turbidity of the samples.

3. The ozone washing system of claim 2, wherein the hydroxyl radical indicator comprises terephthalate.

4. The ozone washing system of claim 2, wherein the hydroxyl radical indicator comprises one or more of 4-hydroxybenzoic acid, salicylate, and phenylalanine.

5. The ozone washing system of claim 2, wherein the hydroxyl radical indicator is sensitive to oxidization in the presence of hydroxyl radicals to form a fluorescent molecule.

6. The ozone washing system of claim 2, wherein the hydroxyl radical indicator is sensitive to oxidization in the presence of hydroxyl radicals while being non-sensitive to oxidization in the presence of ozone.

7. The ozone washing system of claim 2, wherein the filter comprises one or more of a polymer filter, a ceramic filter, and a porous metal filter.

8. The ozone washing system of claim 2, wherein the filter comprises one or more of a PVDF-type polymer filter, a silicon dioxide-type ceramic filter, and a stainless steel-type porous metal filter.

9. The ozone washing system of claim 2, wherein the large molecule sieve comprises one or more sieves of an inorganic sieve and a polymeric sieve.

10. The ozone washing system of claim 2, wherein the large molecule sieve comprises one or more of a silica-type inorganic sieve, an alumina-type inorganic sieve, an ion-exchange resin-type polymeric sieve, a polyAPTAC-type polymeric sieve, a ceramic-type ultra-filtration membrane, a ceramic-type nano-filtration membrane, a PVDF-type polymer ultra-filtration membrane, and a PVDF-type polymer nano-filtration membrane.

11. The ozone washing system of claim 1, wherein the hydroxyl radical sensor further comprises:
    a pump coupled in fluid communication with the washing machine;
    a filter coupled in fluid communication with the pump, the filter configured to reduce turbidity of the samples;
    a large molecule sieve coupled in fluid communication with the filter, the large molecule sieve configured to remove soluble dye molecules from the samples;
    a test chamber coupled in fluid communication with the large molecule sieve, the test chamber configured to receive one or more samples of fluid from the washing machine;
    an indicator reservoir coupled in communication with the test chamber to deliver a hydroxyl radical indicator to the test chamber, wherein the hydroxyl radical indicator is sensitive to oxidization in the presence of hydroxyl radicals; and
    a light source and a detector associated with the test chamber, the light source and detector configured to perform a spectroscopic measurement on the one or more samples of fluid received in the test chamber.

12. The ozone washing system of claim 11, wherein the test chamber comprises a preliminary test chamber configured to hold the one or more samples without the hydroxyl radical indicator for a pre-indicator control measurement, and a primary test chamber configured to hold the one or more samples with the hydroxyl radical indicator for a post-indicator measurement.

13. A hydroxyl radical sensor, comprising:
    a filter configured to reduce turbidity in one or more samples of fluid;
    a large molecule sieve coupled in fluid communication with the filter, the large molecule sieve configured to remove soluble dye molecules from the one or more samples of fluid;
    a test chamber coupled in fluid communication with the large molecule sieve, the test chamber configured to receive the one or more samples of fluid; and
    an indicator reservoir coupled in communication with the test chamber to deliver a hydroxyl radical indicator to the test chamber, wherein the hydroxyl radical indicator is sensitive to oxidization in the presence of hydroxyl radicals;
    wherein the hydroxyl radical sensor is configured to quantify hydroxyl radical levels in the one or more samples of fluid.

14. The hydroxyl radical sensor of claim 13, wherein the hydroxyl radical indicator comprises terephthalate.

15. The hydroxyl radical sensor of claim 13, wherein the hydroxyl radical indicator comprises one or more of 4-hydroxybenzoic acid, salicylate, and phenylalanine.

16. The hydroxyl radical sensor of claim 13, wherein the hydroxyl radical indicator is sensitive to oxidization in the presence of hydroxyl radicals to form a fluorescent molecule.

17. The hydroxyl radical sensor of claim 13, wherein the filter comprises one or more of a PVDF-type polymer filter, a silicon dioxide-type ceramic filter, and a stainless steel-type porous metal filter.

18. The hydroxyl radical sensor of claim 13, wherein the large molecule sieve comprises one or more of a silica-type inorganic sieve, an alumina-type inorganic sieve, an ion-exchange resin-type polymeric sieve, a polyAPTAC-type polymeric sieve, a ceramic-type ultra-filtration membrane, a ceramic-type nano-filtration membrane, a PVDF-type polymer ultra-filtration membrane, and a PVDF-type polymer nano-filtration membrane.

19. The hydroxyl radical sensor of claim 13, further comprising:
  a pump coupled in fluid communication with the filter; and
  a light source and a detector associated with the test chamber, the light source and detector configured to perform a spectroscopic measurement on the one or more samples of fluid received in the test chamber;
  wherein the test chamber comprises a preliminary test chamber configured to hold the one or more samples without the hydroxyl radical indicator for a pre-indicator control measurement, and a primary test chamber configured to hold the one or more samples with the hydroxyl radical indicator for a post-indicator measurement.

20. A method of quantifying hydroxyl radical levels in a washing machine, the method comprising:
  obtaining one or more samples of fluid from the washing machine;
  reducing turbidity, via a filter, in the one or more samples of fluid;
  removing soluble dye molecules, via a large molecule sieve coupled in fluid communication with the filter, in the one or more samples of fluid;
  receiving, via a test chamber coupled in fluid communication with the large molecule sieve, the one or more samples of fluid;
  delivering, via an indicator reservoir coupled in communication with the test chamber, a hydroxyl radical indicator to the test chamber, wherein the hydroxyl radical indicator is sensitive to oxidization in the presence of hydroxyl radicals; and
  quantifying hydroxyl radical levels in the one or more samples of fluid.

21. The method of claim 20, further comprising:
  obtaining a baseline measurement prior to delivery of the hydroxyl radical indicator, wherein the quantification of the hydroxyl radical levels is based at least in part on the taken baseline measurement; and
  inserting ozone, via an ozone reservoir, to the washing machine based at least in part on the quantification of the hydroxyl radical levels.

22. The method of claim 20, wherein the hydroxyl radical indicator is non-toxic and is sensitive to oxidization in the presence of hydroxyl radicals to form a fluorescent molecule.

23. The method of claim 20, wherein the obtaining of the one or more samples of fluid is performed via a pump coupled in fluid communication with the filter and the washing machine, and wherein the quantification of the hydroxyl radical levels is performed via a light source and a detector associated with the test chamber.

24. The method of claim 20, wherein the obtaining of the one or more samples and the quantification of hydroxyl radical levels may be performed at intervals, wherein the intervals are determined based at least in part on a previous quantification of hydroxyl radical levels.

25. An article comprising:
  a signal bearing medium comprising machine-readable instructions stored thereon, which, if executed by one or more processors, operatively enable a computing device to:
  obtain and treat one or more samples of fluid from a washing machine, wherein the treatment includes reducing turbidity via a filter and removing soluble dye molecules via a large molecule sieve;
  deliver, via an indicator reservoir coupled in communication with the test chamber, a hydroxyl radical indicator to the one or more samples of fluid, wherein the hydroxyl radical indicator is sensitive to oxidization in the presence of hydroxyl radicals;
  quantify hydroxyl radical levels in the one or more samples of fluid; and
  insert ozone, via an ozone reservoir, to the washing machine based at least in part on the quantification of the hydroxyl radical levels.

* * * * *

UNITED STATES PATENT AND TRADEMARK OFFICE
CERTIFICATE OF CORRECTION

| | | |
|---|---|---|
| PATENT NO. | : 8,809,064 B2 | Page 1 of 1 |
| APPLICATION NO. | : 13/318398 | |
| DATED | : August 19, 2014 | |
| INVENTOR(S) | : Miller | |

It is certified that error appears in the above-identified patent and that said Letters Patent is hereby corrected as shown below:

On the Title Page

On Page 2, in Item (56), under "OTHER PUBLICATIONS", in Column 1, Line 9, delete "solicylate" and insert -- salicylate --, therefor.

In the Drawings

In Fig. 5, Sheet 5 of 5, below "Processor (510)", Line 1, delete "uP/uC/DSP" and insert -- µP/µC/DSP --, therefor.

In the Specification

In Column 1, Line 9, delete "filed on Mar. 9, 2011," and insert -- under 35 U.S.C. 371 filed on Mar. 9, 2011, --, therefor.

In Column 4, Line 63, delete "hydroxyterephalate" and insert -- hydroxyterephthalate --, therefor.

In Column 4, Lines 65-66, delete "hydroxyterephalate" and insert -- hydroxyterephthalate --, therefor.

In Column 4, Line 1, delete "reservoir 102" and insert -- reservoir 104 --, therefor.

In Column 5, Line 5, delete "500 µM" and insert -- 500 pM --, therefor.

In Column 5, Line 5, delete "500 µM" and insert -- 500 pM --, therefor.

Signed and Sealed this
Twenty-seventh Day of January, 2015

Michelle K. Lee
*Deputy Director of the United States Patent and Trademark Office*